United States Patent [19]

Tran et al.

[11] Patent Number: 5,527,680
[45] Date of Patent: Jun. 18, 1996

[54] METHOD FOR EXTRACTING SOLUTES FROM GEL PLUGS

[75] Inventors: Huu M. Tran, San Jose; Diana M. Smith; Lois B. Epstein, both of Tiburon, all of Calif.

[73] Assignee: The Regents of the University of California, Oakland, Calif.

[21] Appl. No.: 404,687

[22] Filed: Mar. 15, 1995

[51] Int. Cl.⁶ .......................... C12Q 1/00; B01D 57/02; B01D 61/42; C25B 7/00
[52] U.S. Cl. .................... 204/466; 204/462; 204/613; 204/616; 356/344
[58] Field of Search .......................... 204/1.11, 180.1, 204/182.8, 299 R; 356/344; 435/287, 4, 299, 6

[56] References Cited

PUBLICATIONS

Fisher Catalog (1993/4) Fisher Scientific, Pgh PA p. 1193.
*Biotechniques* Lombard–Platet et al., vol. 15 No. 4 pp. 669–672 (1993).
Cooper T., "The Tools of Biochemistry" John Wiley & Sons, (NY) (pp. 194–233) (1977).

*Primary Examiner*—Esther M. Kepplinger
*Assistant Examiner*—Choon P. Koh
*Attorney, Agent, or Firm*—Townsend and Townsend and Crew

[57] ABSTRACT

A flow-through receptacle is disclosed, one end of which is designed to hold multiple plugs of gel material, containing solutes such as macromolecules, excised from electrophoretic separations, and the other end of which is capable of insertion into a recipient matrix that lies between the plates of a slab gel enclosure in an electrophoresis apparatus. The receptacle is used to place the gel plugs, containing the macromolecules or solutes, into electrophoretic contact with a recipient matrix and allows for electrophoretic transfer of the solutes from the plugs into a single concentrated zone in the recipient matrix. The concentrated macromolecules or solutes can then be further processed in the recipient gel or excised and used for procedures requiring greater amounts and concentrations of the solute than are available in the original plugs.

11 Claims, 4 Drawing Sheets

5,527,680

METHOD FOR EXTRACTING SOLUTES FROM GEL PLUGS

GOVERNMENT RIGHTS

This invention was made with Government support under Grant Nos. CA44446 and CA27903, awarded by the National Institutes of Health. The Government has certain rights in this invention.

This invention resides in the field of protein and nucleic acid separations.

This invention resides in the field of protein and necleic acid separations.

BACKGROUND OF THE INVENTION

Advanced research in proteins and the development of increasingly sophisticated uses of proteins for diagnostic and therapeutic purposes have drawn attention to proteins which are available only in very minute amounts. Such proteins are currently of interest for antibody preparations and vaccine preparations as well as clinical techniques such as screening and diagnostic protocols to monitor the presence of the proteins, the clinical course of the proteins, or the response of a patient to therapy. Tissue-specific, tumor-related and viral antigens are examples of proteins where this need is particularly evident.

The most successful means of isolating these minute amounts are the various types of electrophoresis, such as for example one- and two-dimensional polyacrylamide gel electrophoresis. Electrophoresis produces gel spots or bands containing purified protein that can be visualized by different methods, such as autophoresis, staining, and autoradiography. The bands or spots are often faint, however, due to the small amount of protein contained within them, and the quantities contained within any single excised gel piece are usually too small for further processing or for use in most clinical, diagnostic or therapeutic preparations. As a result, the identification of these proteins by microsequencing techniques is limited.

In addition, researchers are often called upon to sequence proteins present in small amounts in biological material. Investigators have reported that digestion can occur more efficiently and reliably in protocols which are performed in situ (i.e., either in a gel or on a blot), as compared to those in which the protein is electroeluted, then concentrated and digested in solution. In situ digestion protocols however are often successful only when the protein is present in a concentration considerably higher than that of the typical band or spot isolated directly from the biological material.

Nucleic acids present similar problems. Procedures such as cloning genes, preparing probes for northern blot analyses, and performing studies relating to the structure and function of DNA often require higher concentrations of nucleic acids than can be directly obtained from electrophoretic separations.

To achieve these higher concentrations in either proteins or nucleic acids, the solutes must be extracted from several excised gel pieces containing the same protein or nucleic acid. This is typically done by electroelution of the solute from multiple gel pieces into buffer followed by concentration using various methods. The recovery of solutes from this two-step process is usually low, however. Alternatively, the solute can be extracted and electrophoretically transferred to a recipient gel. Typical arrangements for performing such an extraction in a slab gel between a pair of glass plates are described in two disclosures. One of these is Rasmussen, H. H., et al., "Protein-electroblotting and microsequencing in establishing integrated human protein databases" (in Methods in Protein Sequence Analysis, pp. 103–114, Jornvall, H. V., et at., eds., Advances in life Sciences, Birkauser, Denmark, 1991). Rasmussen, et al. disclose the preparation of a well which is wide enough to accommodate a large number of gel pieces and is formed at the top of a slab gel by inserting four spacers a few centimeters into the gel at the center of the top edge of the gel with adjacent side edges of the spacers touching. The two inner spacers are then removed to leave the well laterally bounded by the remaining two spacers. The well and the two remaining spacers occupy a significant part of the gel volume and the method requires the user not only to use additional spacers but also to attach the spacers to the glass plates enclosing the gel and secure them in position. The other disclosure is Lombard-Platet, G., et al., "Funnel-well SDS-PAGE: a rapid technique for obtaining sufficient quantities of low-abundance proteins for internal sequence analysis," Biotechniques 15:668–672 (1993). Lombard-Platet, et al. use spacers which are specially shaped to fill in the entire volume between the two glass plates except for a single funnel-shaped well. The upper portion of the well is a wide-angle inverted triangle and the lower portion is a straight vertical channel 5 mm in width. Resolving and stacking gels are poured through the triangular section into the vertical channel, leaving the triangular section open. The gel pieces are then placed in the triangular section above the gel, which is then filled with buffer. As the voltage is applied, the proteins migrate downward and are concentrated into the 5 mm channel. This arrangement requires specially constructed spacers and consumes the entire width of the gel.

SUMMARY OF THE INVENTION

The present invention resides in a receptacle for use with a conventional slab gel for concentrating and consolidating small quantities of solute from multiple pieces of gel material, and a method for using the receptacle with a conventional slab gel and slab gel electrophoresis cell. The receptacle requires no additional or strategically placed spacers and occupies such a small portion of the typical slab gel that several such receptacles can be used at the same time, permitting multiple concentrations to be performed simultaneously and independently.

The receptacle is a flow-through receptacle with a section at one end sufficiently large to accommodate many pieces of gel material such as those excised from preparative gels. The latter end of the receptacle can be made of a width small enough to fit within the wells formed by conventional well-forming inserts or "combs" of the gel matrix that is cast between the plates of a conventional slab gel apparatus, currently available from suppliers of laboratory equipment. This latter end is partially compressed or flattened to fit snugly within the well.

In preferred embodiments of the invention, the receptacle is a composite tube which includes two sections of different diameters, the larger diameter section serving to retain the gel pieces and the small diameter section being of resilient construction so that it can be flattened to fit between the flat plates of the cell. Depending on its size, the large diameter section can accommodate five, ten, or fifty or more pieces of gel material. In still further preferred embodiments, these two sections are joined by a frustoconical (i.e., tapering) section to provide a smooth transition and flow path for the solutes, avoiding dead space.

DETAILED DESCRIPTION OF THE INVENTION AND PREFERRED EMBODIMENTS

Figure 1:
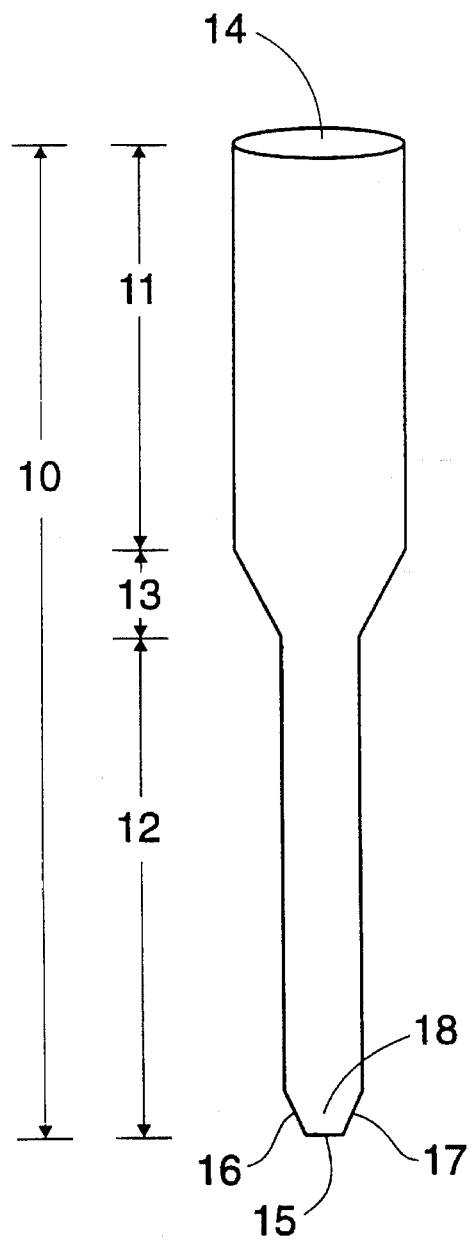
FIG. 1 is a side view of a flow-through receptacle in accordance with the present invention.

While this invention can be implemented in a variety of ways and embodied in variety of structures and arrangements, the following description will focus on the device shown in the drawings, which represents one example of the invention.

Figure 2:
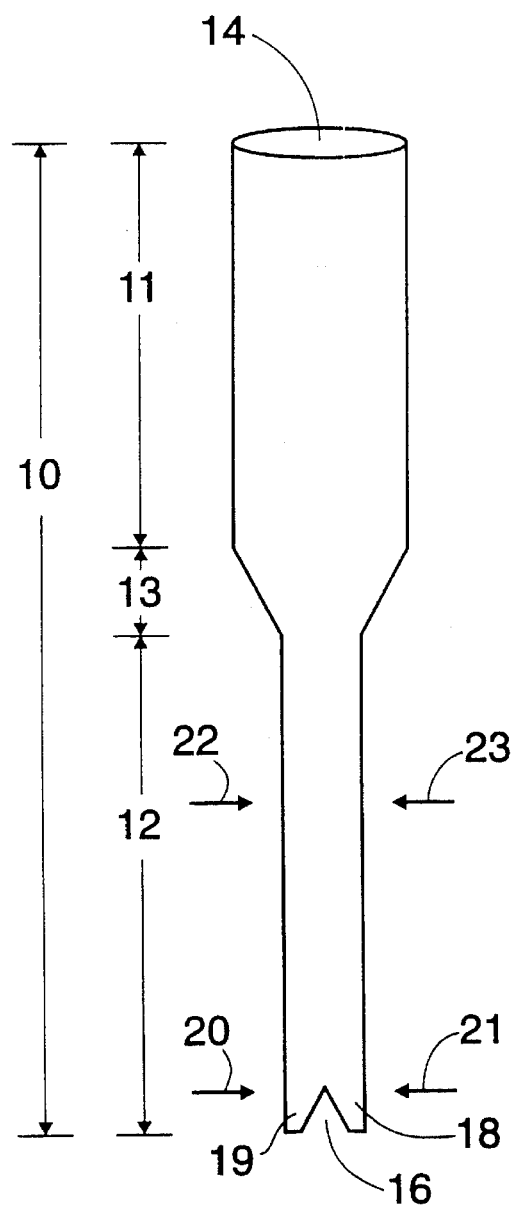
FIG. 2 is a further side view of the receptacle shown in FIG. 1, rotated 90° around the longitudinal/axis.

FIGS. 1 and 2 show two views, one rotated 90° relative to the other, of a composite tube 10 serving as a receptacle in accordance with the present invention. The receptacle consists of two circular cylindrical sections 11, 12, separated by a transitional region section 13, with openings only at the top 14 and bottom 15. The lower cylindrical section 12 is deformable but resilient, so that it can be flattened by moderate manual pressure but will return to its circular cross section upon release of the pressure. The upper cylindrical section 11 may be manufactured of the same material, but any deformability will be incidental and this section will not generally be deformed in the practice of the invention. In the embodiment shown in these Figures, these two sections 11, 12 are coaxial right circular cylinders of two different diameters, while the transitional region is frustoconical, or any other shape that provides a smooth transition between the dissimilar diameters of the upper and lower cylindrical sections.

A pair of notches 16, 17 are cut in the bottom end of the lower cylindrical section on opposing sides, dividing the lower end of the tube into a pair of opposing tabs 18, 19. These tabs can be pressed together by the user as indicated by the arrows 20, 21, to flatten the lower end of the tube and thereby facilitate its insertion into a well of the gel that is cast between the two glass plates of the slab gel enclosure (not shown in FIG. 1). The remainder of the lower cylindrical section 12 can then be pushed down into the space between the plates into an appropriate well. As this is occurring, the plates will compress the tube as indicated by the arrows 22, 23, into a flattened or partially flattened condition. Therefore, the lower end of the tube will fit snugly into the well of the gel. The resiliency of the tube and the pressure its sides exert against the glass plates will hold the tube in place.

The dimensions of the various sections of the composite tube and the materials from which it is made are not critical other than with the above considerations in mind, as well as considerations such as the size and number of gel pieces intended to be placed in the upper section. The gel pieces are placed in the upper section of the device after the lower section has been inserted in a well of a gel between the two plates.

In preferred embodiments of the invention, the internal volume of the upper cylindrical section 11 will be at least about 1 cubic centimeter, more preferably from about 1 to about 20 cubic centimeters, and most preferably from about 3 to about 10 cubic centimeters. In one example constructed and tested by the inventors herein, the upper cylindrical section and the transition region was a section cut from a polyethylene transfer pipette 13 mm in diameter, and the lower cylindrical section was cut from a polypropylene straw 7 mm in diameter, the two parts glued together with an inert, heat-resistant, waterproof glue. The upper section 11 was approximately 32 mm in length, the lower section 12 (including the tabs 18, 19) approximately 37 mm in length, the transitional region 13 approximately 6 mm in length, the notches 16, 17 approximately 4 mm deep and 5 mm wide at their bases.

Figure 3:
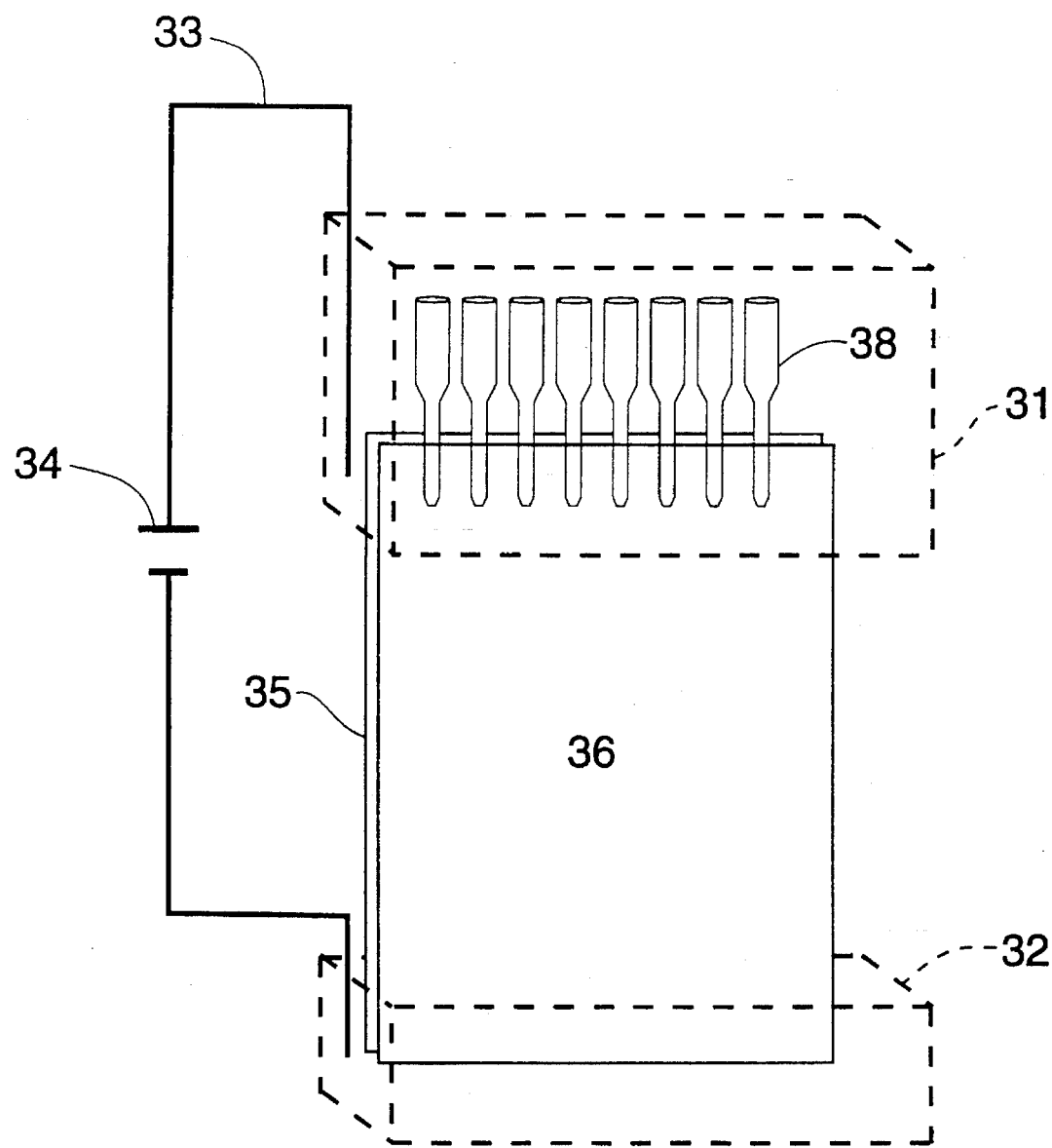
FIG. 3 is a perspective view of a slab gel apparatus with receptacles of the type shown in FIGS. 1 and 2 inserted, and with other elements of an electrophoresis cell.

FIG. 3 shows eight of the composite tubes in position in the top of a slab gel, ready for the extraction and concentration of proteins from the gel pieces. The Figure also shows the rudimentary features of a slab gel electrophoresis cell, including the upper 31 and lower 32 buffer chambers in dashed lines, the electric circuit 33, the power source 34 and the two glass plates 35, 36 separated by a gap of fixed width which is occupied by the gel. In this arrangement, eight composite tubes 38 are shown. Thus, eight different proteins can be extracted simultaneously from multiple pieces of gel material, each into a single concentrated zone in the recipient slab gel residing between the glass plates. Note that the top openings 14 of the composite tubes are fully immersed in the upper buffer solution. The electric circuit thus passes through each of the composite tubes and down through the slab gel.

Figure 4:
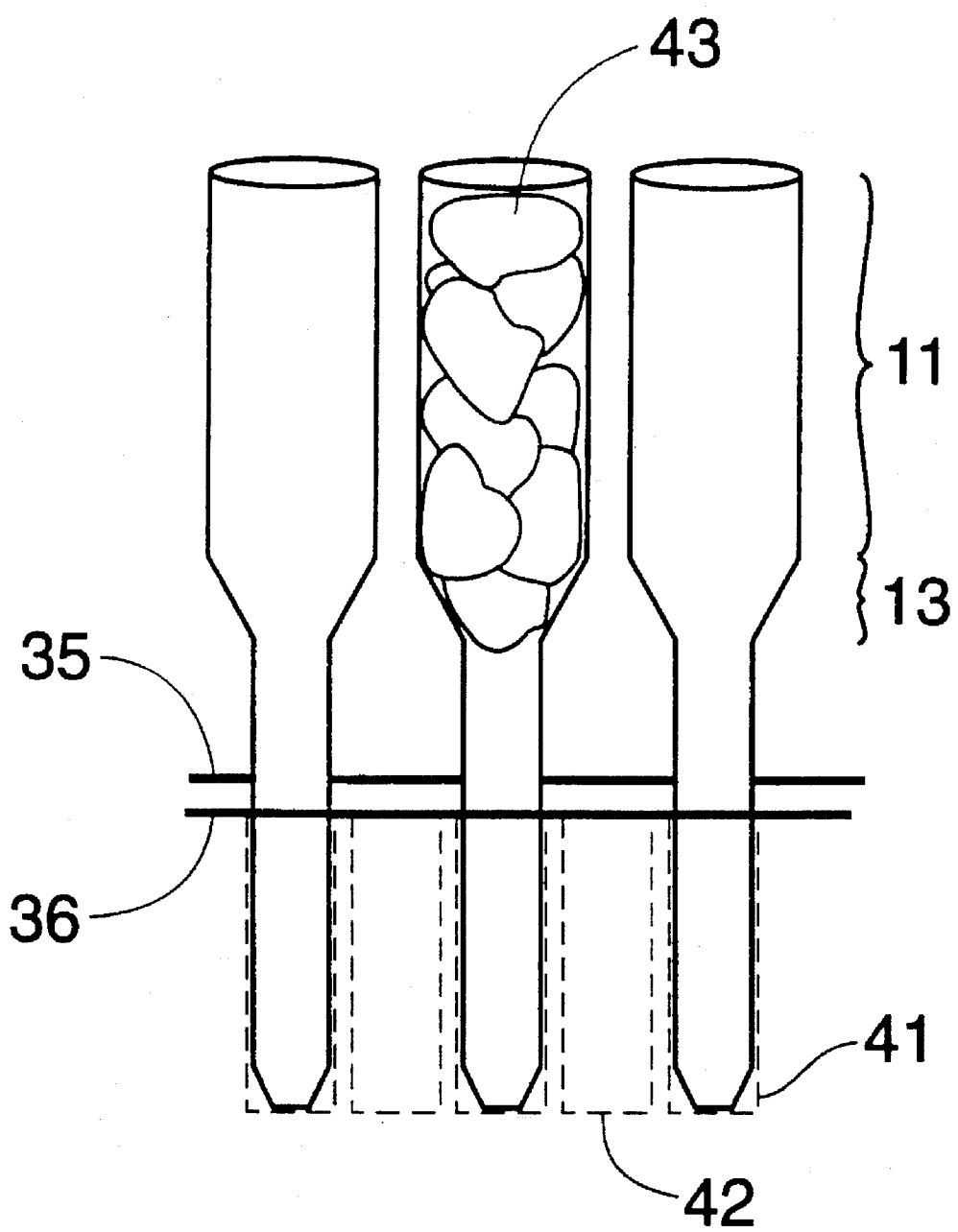
FIG. 4 is an enlarged view of three receptacles of the type shown in the preceding Figures, inserted into the wells of a gel that is cast between the two glass plates of the slab gel enclosure.

FIG. 4 offers an enlarged view of the upper edges of the glass plates 35, 36 with the gel in between and three of the composite tubes 38 inserted between the plates. The gel occupying the space between the plates has been formed with a well-forming insert (or "comb" in the parlance of the industry), which was removed once the gel material polymerized, leaving a series of wells 41, 42 in the upper edge of the gel. In this case, a composite tube 38 has been placed in every other well 41, with the intervening wells 42 left unoccupied. The pieces of gel material 43 fill the upper section 11 as well as the transitional region 13 of the central composite tube.

The composition of the gel is not critical to the invention, and will vary depending on the needs of the particular extraction being performed, such as the type of solute and perhaps the type of gel from which the solute is being extracted. Conventional electrophoresis gel materials, such as agarose or crosslinked polyacrylamide, containing a denaturing agent, can be used. It is convenient to use a dual-layer gel consisting of a resolving gel with a stacking gel above it. The resolving gel is typically of a higher (often double, for example) concentration of gel material relative to the stacking gel. In general, conditions and procedures for performing the electrophoresis are conventional.

To obtain best results, the gel pieces are pretreated prior to their placement in the composite tube, to equilibrate the gel pieces to the pH at which the extraction is to be performed. Denaturing agents can also be included in the pretreatment medium, as well as dyes or pigmented solutes which can be used to monitor the migration rate.

This invention is applicable to gel pieces of a variety of configurations (shapes and sizes) and from a variety of sources. Examples are gel plugs cut from slab gels in which electrophoretic separations have been performed, including both one-dimensional and two-dimensional separations, and pulsed field and oscillating field separations. Further examples are gel plugs cut from tube gels, and any other geometry. The plugs are excised from the original gels with a scalpel or in any conventional manner.

Once the concentration and consolidation of the solutes is performed and a single band or zone containing the solute is obtained, the solute can be processed in the gel or removed from the band in any conventional manner. The concentrated solute is then ready for therapeutic or diagnostic use in its concentrated form, or for sequencing, derivatization, or any other kind of further processing which would benefit from the higher concentration.

The following examples are offered for purposes of illustration, and are intended neither to limit nor to define the invention in any manner.

EXAMPLE 1

The composite tubes (referred to in these examples as "flumes") whose specific materials and dimensions are given above were used for the extraction and consolidation of carbonic anhydrase (CA), a 30-kDa human protein, in various quantities from acrylamide gel plugs. The CA was obtained from Sigma Chemical Co., St. Louis, Mo., U.S.A.

A slab gel of sodium dodecyl sulfate polyacrylamide was prepared in the conventional manner, the total gel measuring 24 cm in length, 18 cm in width and 1.5 mm in thickness. The resolving (lower) portion of the gel was 12% (by weight) acrylamide and 13–15 cm in height, and the stacking portion was 6% acrylamide and 8–10 cm in height. The stacking gel was cast with a comb to form wells approximately 8 mm wide and 25 mm deep. The composite tubes were positioned as shown in the Figures.

The acrylamide gel plugs, each containing 1 µg of CA, were each equilibrated three times for ten minutes each with 3 mL of an equilibration buffer containing 0.5M tris(hydroxymethyl)aminomethane ("Tris") pH 9, 10 mM dithiothreitol, 10% glycerol, and 0.001% bromphenol blue. After equilibration, the buffer was decanted, and the gel plugs were heated for 5 minutes at 65° C., then placed in the upper sections of the flumes, with each flume containing a different number of gel pieces.

The electrophoresis cell used in the experiments was a "Sturdier SE-140" electrophoresis chamber obtained from Hoefer Scientific Instruments, San Francisco, Calif., U.S.A. The running buffer used to perform the extraction was a standard Laemmli loading buffer containing 25 mM Tris (pH 8.8), 192 mM glycine, 0.1 mM sodium thioglycolate and 0.1% SDS (sodium dodecyl sulfate). Electrophoresis was conducted at 100 V for the first thirty minutes, followed by 200–250 V for the remainder of the time necessary for resolution of the protein (5–7 hours). Following electrophoresis, the resolving gel was stained with Coomassie blue G-250 and quantitated by laser densitometry, using a Computing Densitometer, ImageQuant software, Molecular Dynamics, Sunnyvale, Calif., U.S.A.

Table I shows the quantitation of CA resulting from each of four flumes, the flumes containing total CA loadings of 7.5, 15, 30 and 60 µg (in 7.5, 15, 30 and 60 gel pieces). One flume was charged with 7.5 µg of the free protein for comparison. The data in the table indicates that the recovery of protein from the gel plugs was nearly complete (96%) for 7.5 plugs, and that efficient recovery was achieved from all flumes, including that containing 60 pieces.

TABLE I

Quantitation of Carbonic Anhydrase Recovered From Acrylamide Gel Plugs

| | Total protein loaded (µg) | Number of gel plugs loaded | Total optical density of resolved recipient gel spot |
|---|---|---|---|
| Free protein: | 7.5 | — | 2642 |
| Protein in | 7.5 | 7.5 | 2535 |
| gel plugs: | 15 | 15 | 4163 |
| | 30 | 30 | 6340 |
| | 60 | 60 | 9476 |

EXAMPLE 2

Figure 5:
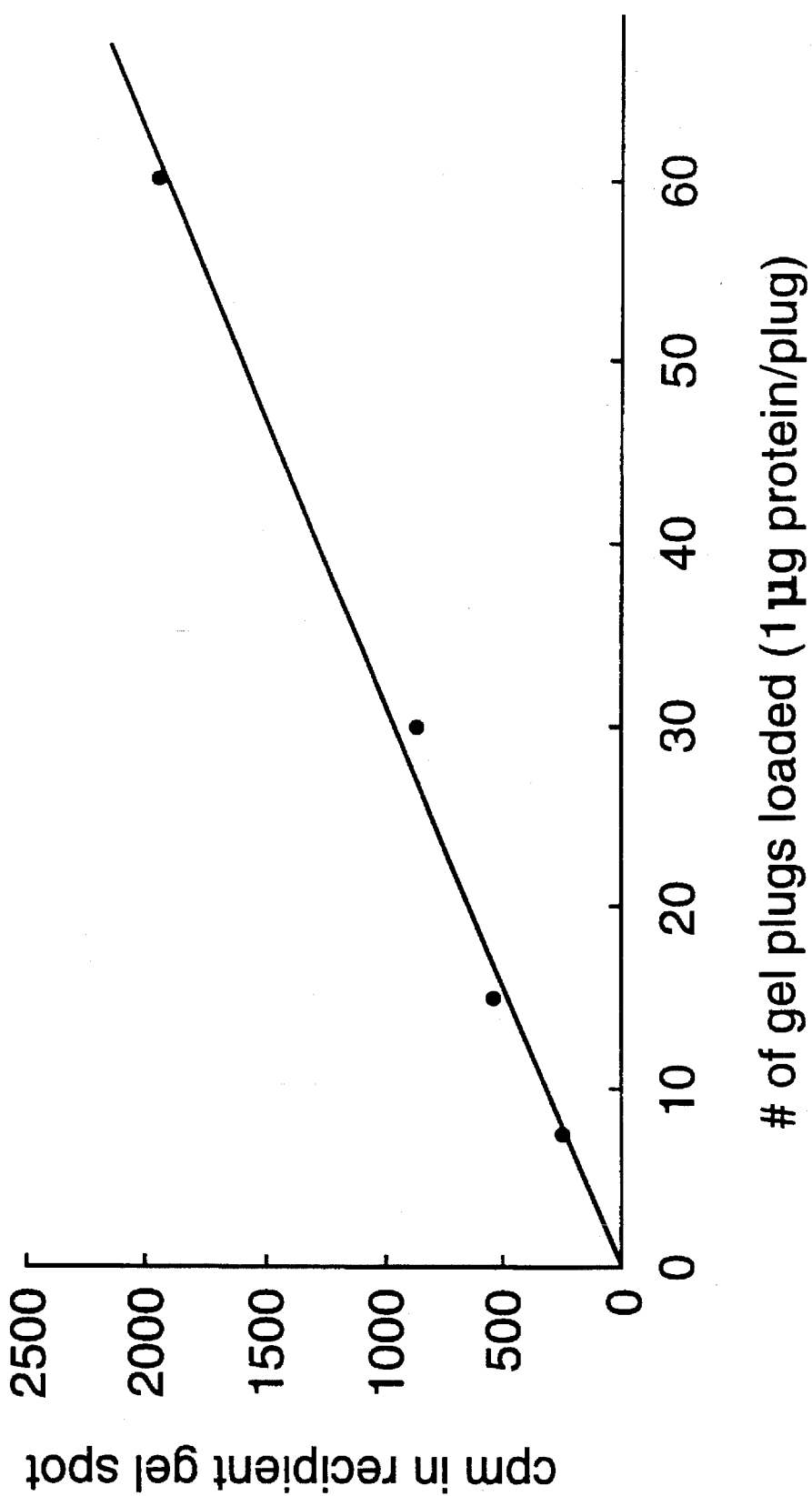
FIG. 5 is a plot of the amount of solute recovered in a concentrated zone in accordance with the invention vs. the amount of solute present in the gel plugs from which the solute was extracted.

An experiment similar to that of Example 1 was conducted, this time however using CA spiked with 1800 dpm of $^{14}$C-labeled CA from New England Nuclear, Cambridge, Mass., U.S.A. After electrophoretic extraction from each of the flumes, the protein spots were excised from the resolving gel and the amount of radioactivity from each spot was measured in a scintillation counter. Table II below and FIG. 5 show the quantitative recovery in terms of counts per minute vs. the amount of protein in the flumes.

TABLE II

Quantitative Recovery of $^{14}$C-Labeled Carbonic Anhydrase From Acrylamide Gel Plugs

| Quantity of protein in flume (µg) | Number of gel plugs loaded | cpm resolved in recipient gel spot |
|---|---|---|
| 7.5 | 7.5 | 250 |
| 15 | 15 | 533 |
| 30 | 30 | 877 |
| 60 | 60 | 1978 |

The data in Table II and FIG. 5 indicate that the recovery is a linear (correlation coefficient 0.996) function of the amount originally charged to the flumes.

EXAMPLE 3

A "flume" such as that used in the preceding examples was used to concentrate a 20 kDa, 5.6 pI cytokine-induced melanoma protein isolated from fifty preparative two-dimensional polyacrylamide gels. Following the procedures of the preceding examples, the protein was resolved into a single band in the resolving gel, and the band was then excised from the gel for recovery of the protein. Sufficient protein was obtained from the excised band to allow the sequencing of this protein by sequencing methods involving CNBr digestion, subsequent electrophoretic separation of peptide fragments, electroblotting and automated Edman degradation. The partial amino acid sequence obtained was homologous to an N-terminal fragment of the alpha chain of tubulin, and its identity was confirmed by immunoblot analysis.

This demonstrates that the flume resolved and concentrated small amounts of the protein from the fifty acrylamide gel plugs to achieve an amount sufficient for microsequencing and identification, and did so in an efficient and reliable manner.

Similar experiments were performed with another protein (human high mobility group chromosomal protein-1). This protein was extracted from two-dimensional polyacrylamide gel electrophoresis gel plugs, and concentrated in the same manner as described in preceding examples. Twenty-four such plugs were used in one procedure and ten in another. In both cases, the extracted protein was concentrated in a single band in the recipient resolving gel, and the band was then excised for further processing, sequencing and analysis. Successful sequencing permitted the identification of the protein based on homology between its amino acid sequence and that of proteins characterized previously and catalogued in a Protein Identification Resource data base compiled by George, D. C., et al., Nucleic Acids Research 14:11–15 (1986). This once again demonstrated that the flume successfully resolved and concentrated the protein so that it could be sequenced.

The foregoing is offered primarily for purposes of illustration. It will be readily apparent to those skilled in the art that the materials, dimensions, operating conditions, procedural steps and other parameters of the invention described herein may be further modified or substituted in various ways without departing from the spirit and scope of the invention.

What is claimed is:

1. A method for extracting solute suspended in a plurality of pieces of gel material and concentrating solute so extracted, said method comprising:

(a) providing a flow-through receptacle having a lower end capable of fitting inside a slab gel enclosure and an upper end capable of receiving at least about 1 cubic centimeter of gel material;

(b) providing a slab-shaped gel retained between a pair of flat plates, said slab-shaped gel having an upper edge with a plurality of wells formed therein capable of receiving said lower end of said receptacle;

(c) placing said lower end of said receptacle inside one of said wells and said pieces of gel material in said upper end of said receptacle;

(d) passing electric current through said receptacle and said slab-shaped gel to cause electrophoretic migration of a given solute into a zone in said slab-shaped gel in which said solute has migrated and thus become concentrated; and (e) recovering said zone from said slab-shaped gel.

2. A method in accordance with claim 1 in which said upper end of said flow-through receptacle has an internal volume of from about 1 cubic centimeter to about 20 cubic centimeters.

3. A method in accordance with claim 1 in which said upper end of said flow-through receptacle has an internal volume of from about 3 cubic centimeters to about 10 cubic centimeters.

4. A method in accordance with claim 1 in which said slab gel enclosure comprises a pair of flat plates with a gap therebetween defining a thickness for said slab-shaped gel, said lower end of said flow-through receptacle is a resilient tube which when relaxed has a diameter exceeding the width of said gap, and step (c) comprises flattening said resilient tube to fit inside said gap.

5. A method in accordance with claim 4 in which step (c) comprises flattening said resilient tube from an outer diameter exceeding about 5.0 mm to a flattened form having a thickness of less than about 3.0 mm.

6. A method in accordance with claim 1 in which step (c) comprises placing at least five pieces of said gel material in said upper end of said receptacle.

7. A method in accordance with claim 1 in which step (c) comprises placing at least five pieces of said gel material in said upper end of said receptacle.

8. A method in accordance with claim 1 in which step (c) comprises placing at least fifty pieces of said gel material in said upper end of said receptacle.

9. A method in accordance with claim 1 in which step (d) is performed with said slab-shaped gel at a selected pH, said method further comprising treating said pieces of gel material prior to step (c) to preequilibrate said pieces of gel material to said selected pH.

10. A method in accordance with claim 1 in which step (d) is performed with said slab-shaped gel at a selected pH, said method further comprising preequilibrating said pieces of gel material to said selected pH prior to step (c), and heating said gel pieces prior to step (d) to at least partially denature and facilitate the electrophoresis of any protein contained in said solute.

11. A method for extracting a plurality of solutes suspended in a plurality of pieces of gel material and concentrating solutes so extracted, said method comprising:

(a) providing a plurality of flow-through receptacles, each having a lower end capable of fitting inside a slab gel enclosure and an upper end capable of receiving at least about 1.0 cubic centimeter of gel material;

(b) providing a slab-shaped gel retained between a pair of flat plates, said slab-shaped gel having an upper edge with a plurality of wells formed therein, each well capable of receiving said lower end of one of said receptacles;

(c) placing said lower ends of said receptacles inside separate wells and said pieces of gel material in said upper ends of said receptacles with one solute per receptacle;

(d) passing electric current through said receptacles and said slab-shaped gel to cause electrophoretic migration of said solutes into zones in said slab-shaped gel in which said solutes have migrated and thus become concentrated, with one solute per zones; and (e) recovering said zone from said slab-shaped gel.

* * * * *